United States Patent [19]
Öhman

[11] Patent Number: 5,443,890
[45] Date of Patent: Aug. 22, 1995

[54] METHOD OF PRODUCING A SEALING MEANS IN A MICROFLUIDIC STRUCTURE AND A MICROFLUIDIC STRUCTURE COMPRISING SUCH SEALING MEANS

[75] Inventor: Ove Öhman, Uppsala, Sweden

[73] Assignee: Pharmacia Biosensor AB, Uppsala, Sweden

[21] Appl. No.: 90,119

[22] PCT Filed: Feb. 4, 1992

[86] PCT No.: PCT/SE92/00062
§ 371 Date: Jul. 22, 1993
§ 102(e) Date: Jul. 22, 1993

[87] PCT Pub. No.: WO92/14132
PCT Pub. Date: Aug. 20, 1992

[30] Foreign Application Priority Data

Feb. 8, 1991 [SE] Sweden ................................ 9100392

[51] Int. Cl.[6] .......................... B32B 3/28; B28B 5/00; D01D 5/20
[52] U.S. Cl. .................................... 428/167; 428/166; 428/172; 264/167; 264/241; 264/297.1
[58] Field of Search ............... 428/156, 167, 172, 119, 428/120, 132, 137, 141, 166, 192, 213, 450; 264/510, 513, 167, 241, 297.1

[56] References Cited

U.S. PATENT DOCUMENTS

| | | | |
|---|---|---|---|
| 4,582,684 | 4/1986 | Vogel et al. | 422/57 |
| 4,810,658 | 3/1989 | Shanks et al. | 436/172 |
| 4,880,752 | 11/1989 | Keck et al. | 435/7 |
| 4,978,503 | 12/1990 | Shanks et al. | 422/58 |

OTHER PUBLICATIONS

Intl Publication of WO 90/05295–17 May 1990.

Primary Examiner—Donald J. Loney
Attorney, Agent, or Firm—Birch, Stewart, Kolasch & Birch

[57] ABSTRACT

A leakage-proof sealing means is provided in a microfluidic channel assembly of the type having first and second flat surface members which when pressed against each other define a microfluidic channel system between them, by recessing a sealing groove structure into the flat surface of the first member, and applying against the first member a counter mould surface having an aligned groove and/or ridge structure of smaller width than the sealing groove structure to define a mould cavity therewith, into which a fluid sealing material is introduced and hardened to form a resilient seal, the top part of which projects above the edges of the sealing groove structure while leaving sufficient space in the upper part thereof to permit complete accommodation of the top part of the resilient seal when compressed by the second assembly member.

15 Claims, 6 Drawing Sheets

METHOD OF PRODUCING A SEALING MEANS IN A MICROFLUIDIC STRUCTURE AND A MICROFLUIDIC STRUCTURE COMPRISING SUCH SEALING MEANS

FIELD OF THE INVENTION

The present invention relates to a method for the production of sealing means in microfluidic type assemblies, and to a microfluidic assembly or a member thereof having such sealing means.

BACKGROUND OF THE INVENTION

In one type of microfluidic system the conduit system is defined by micro-sized grooves or channels made in a first plate member and covered by a second flat plate member applied against the first plate member. A conventional material for the plate members is silicon. For the provision of adequate sealing between such silicon members in order to prevent fluid leakage between adjacent conduits or conduit portions, the plate members are bonded to each other, e.g. by glueing, anodic bonding or heating, to make the contact surfaces fuse together. Such a microfluidic silicon structure permits extremely small conduit dimensions, e.g. as low channel heights as 1 micrometer or even less.

For certain applications, however, it is required that the two plate members defining the microfluidic system are not permanently bonded together but may be repeatedly brought apart and put together, respectively. One such application is disclosed in, for example, WO 90/05295 relating to an optical biosensor system based upon surface plasmon resonance (SPR) and comprising a set of microfluidic flow cells for contacting the sample fluid with a sensing surface. Upwardly open flow-through cell channels are recessed into the surface of one plate member and closed by a second plate member supporting the sensing surface on the side thereof facing the first plate member. To provide for the necessary mutual sealing of the flow cells defined between the two plates when pressed together (conventional sealing means of the o-ring type or the like not being feasible in microscale connections) the upwardly open flow cell channels are formed as precision-cast cuts or slits extending through a top layer of an elastomeric material integral with the first plate member. Thereby efficient sealing is obtained when the sensing surface member is pressed against the elastomeric layer and a relatively large number of such dockings may be performed with retained sealing effect. With such an elastomeric layer channel heights as small as 50 micrometers may be provided, a practical lower limit being about 20 micrometers. Channels of still smaller heights may, however, not be made with adequate accuracy.

It has now been found that for obtaining optimum mass transfer conditions in, for example, the above mentioned biosensor application in order to obtain faster analyses and/or a higher sensitivity and/or a more reagent-saving system and/or more accurate kinetic measurements, it would be desired to use a maximum flow cell height of about 10 micrometers. While the desired low height channels, as mentioned above, can be performed in hard materials like silicon, there has so far been no satisfactory solution to the sealing problem associated with non-resilient materials.

SUMMARY OF THE INVENTION

The object of the present invention is to provide a solution to this sealing problem in order to permit inter alia a two-part microfluidic system device of the above mentioned type to be produced in a hard or non-resilient material such as silicon.

In accordance with the present inventive concept an efficient sealing strip may be accomplished by moulding into a channel structure recessed into one of the two plate members to be combined, a resilient sealing material such that the top part of the sealing strip formed projects above the groove structure edges, and has such a configuration in the upper part of the groove structure that, when the sealing strip is compressed by pressing of the two plate members against each other, the deformed material is capable of being completely accommodated in the upper part of the groove structure. Such a sealing strip may be produced in the necessary small size and will permit complete contact between the non-recessed areas of the plate members while simultaneously providing efficient leakage-proof sealing between areas on either sides of the sealing strip. A sealing strip produced in the described manner will be excellently useful for microfluidic purposes, and particularly when very small channel heights are involved.

Thus, in one aspect the present invention provides a method for producing a leakage-proof sealing means in a microfluidic channel assembly comprising first and second flat surface members which when pressed against each other define at least part of a microfluidic channel system between them, which method comprises the steps of (i) recessing at least one groove structure into the flat surface of the first member;
(ii) providing a counter mould, the mould surface of which has at least one groove structure or at least one ridge structure, optionally in combination, said structure or structures having a corresponding extension as, but a smaller width than the groove structure or structures of the first member;
(iii) applying the counter mould against the first member such that a mould cavity or cavities are defined by the groove structure or structures of the first member with the counter mould surface portions comprising said groove or ridge structure or structures;
(iv) introducing, e.g. injecting, a fluid sealing material capable of hardening to form a resilient sealing structure into the mould cavity or cavities; and
(v) after hardening of the fluid sealing material removing the mould from the first member;

the top part of the mould cavity or cavities being configured in dependence of the shrinkage or expansion properties of the fluid sealing material such that the resulting moulded resilient sealing structure projects above the groove edges of the first member while leaving sufficient space in the upper part of the groove to permit complete accommodation therein of the deformed top part of the resilient sealing structure when compressed by the second member.

The term "channel" or "channel system" as used herein is to be interpreted in a broad sense. It is thus not restricted to elongate configurations but is meant to comprise fluid cavities of any desired shape. Such a fluid cavity may, for example, be a flow-through cell which is to be continuously passed by a fluid, but it may also be a chamber for holding a desired fluid volume for a certain time. A fluid channel system may comprise several such channels or cavities which may be separate or interconnected.

By the term "microfluidic" as used herein is usually to be understood, without any restriction thereto, however, fluid structure widths or depths of below about 500 micrometers.

The sealing means may have any desired configuration as long as they will serve the purpose of sealing off one area of the contact surface of the microfluidic assembly members from another. Preferably, the sealing means will completely enclose a fluid channel to prevent fluid leakage in any direction from the channel. Generally the microfluidic assembly will comprise several separate channels and the sealing means will then form one or more sealing structures isolating each channel from another. Optionally, for example, two adjacent sealing means may be provided for increased security.

While the two members of the fluid assembly which together define the fluid system in question between them generally are plate-shaped, they may have any other configuration as long as they exhibit a flat contact surface for defining the channel system with the other assembly member.

The channel system to be isolated by the sealing means may be provided as a groove structure in one of the two assembly members, which groove structure together with the flat surface of the other member will define the channel system. Alternatively, but perhaps not so attractive from the viewpoint of manufacture and assembly, complementary groove structures may be provided in the two members, these groove structures together defining the channel system.

The sealing means may be provided in either of the two members forming the microfluidic assembly. Preferably, however, the sealing means are provided in the same assembly member as that carrying the channel system to be sealed off by the sealing means.

As mentioned above, the sealing means provided by the method of the invention will be provided as a basal part situated in a groove structure, said basal part having projecting therefrom a top portion which upon deformation when the two assembly members are combined will be accommodated in the groove structure. Generally this projecting portion will have the form of a ridge or the like provided substantially centrally in the basal part. It is, however, within the scope of the invention to provide two or more adjacent ridge structures extending from the same basal part.

Generally, the fluid sealing material injected into the mould cavity will exhibit a slight contraction or shrink upon hardening. Such shrink will normally be sufficient for providing the necessary space in the upper part of the sealing material groove for permitting the projecting part of the hardened sealing means to be completely received therein when deformed. The extent of the shrinkage may inter alia be controlled by selecting the depth or height of the groove properly, i.e. a greater depth will give a greater vertical shrinkage and thereby a larger resulting space or spaces in the upper part of the sealing material groove.

In the case, however, that the sealing material will not by itself provide for the desired shrinkage or even expand during the curing, the required space or spaces in the groove top may be effected by configuring the counter mould surface accordingly to provide such space, for example, by forming an elevated strip or ridge portion on either side of the mould groove to occupy the upper side portions of the corresponding sealing material groove structure; in the case of an expanding material no groove structure in the counter mould will, of course, be necessary but only such strips or ridges.

The fluid material for forming the resilient sealing means may, for example, be an elastomer-forming material, such as a silicone rubber, an elastic epoxy resin or fluorocarbon polymer. At present a silicone rubber is considered to be a particularly suitable material for the purposes of the invention.

The material member carrying the channel system may be any hard or rigid material permitting the channel system to be produced therein by per se conventional techniques, such as chemical or electrochemical etching, laser processing, etc. Exemplary of such materials are silicon, ceramics, metals and plastics. Suitably such a hard member is of silicon, the different channel structures being produced by chemical etching.

Advantageously, the groove structure for the sealing means is produced in connection with that of the channel system, e.g. simultaneously, as will be illustrated below in the detailed description of the invention.

In another aspect the present invention provides a microfluidic device comprising one or more sealing means of the type described above. Such a microfluidic device therefore comprises a first member having a substantially flat surface designed to be applied to a second member having a substantially flat surface, which surfaces when pressed against each other define at least part of a microfluidic channel system between them. One of the first and second members additionally comprises a groove structure supporting a resilient sealing material structure, part of which projects above the surface of that member. In accordance with the above this resilient structure is configured such that, when the two members are applied against each other, the resilient material is compressed to permit the flat surfaces of the first and second members to contact each other while providing adequate sealing between areas on either side of each resilient material structure.

As already mentioned previously a suitable material for the sealing material is liquid silicone rubber which may be cross-linked by appropriate cross-linking means, e.g. by incorporating an initiator, or by other means such as UV-light, electron beam curing, etc.

In one embodiment the microfluidic device provided by the present invention comprises both the assembly members which together define the channel system between them. One of the members may then contain the channel system, which at least partially may be in the form of a groove structure or structures arranged to be closed by the flat surface of the second member to complete the channel system. Depending on the contemplated use of the microfluidic device it may further comprise additional channels or conduits, valve means etc. As mentioned above the sealing means may be provided in either of the two members, but preferably in the one carrying the channel system.

In another embodiment the microfluidic device of the invention comprises only the assembly member carrying the channel system and the sealing means, whereas the flat surface necessary to complete the channel system and compress the sealing means is provided as a separate member. One of the members may then form part of, for example, an instrument or apparatus in which the microfluidic device is to be used. An example of the latter case is the use for the previously mentioned optical biosensor application, for example as disclosed in the aforementioned WO 90/05295 where the member containing the channel system and, in accordance with the present invention, also the sealing means, is stationarily provided in the biosensor instrument while the above mentioned flat surface member supports the sensing surface and is in the form of an exchangeable sensor chip insertable into the instrument to dock with the first member.

In the WO 90/05295 publication there is also described a method of monitoring the temperature at the sensing layer. According to this method one or more of the sealing areas between the flow channels are coated with or consist of a dielectric having a known temperature dependence of its refractive index, the latter being within the detection range of the instrument. The signal representing the resonance angle as measured at the sealing areas between the flow channels will then represent an actual temperature value at the dielectric layer. By applying the present invention and selecting the sealing material properly with regard thereto the resilient sealing material areas in the present microfluidic system device may well serve such purpose as a temperature reference. Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in more detail by way of a specific embodiment, reference being made to the accompanying drawings which are given by way of illustration only, and thus are not limitative of the present invention, and wherein.

DETAILED DESCRIPTION OF THE PREFERRED EMBODIMENTS

Figure 1:
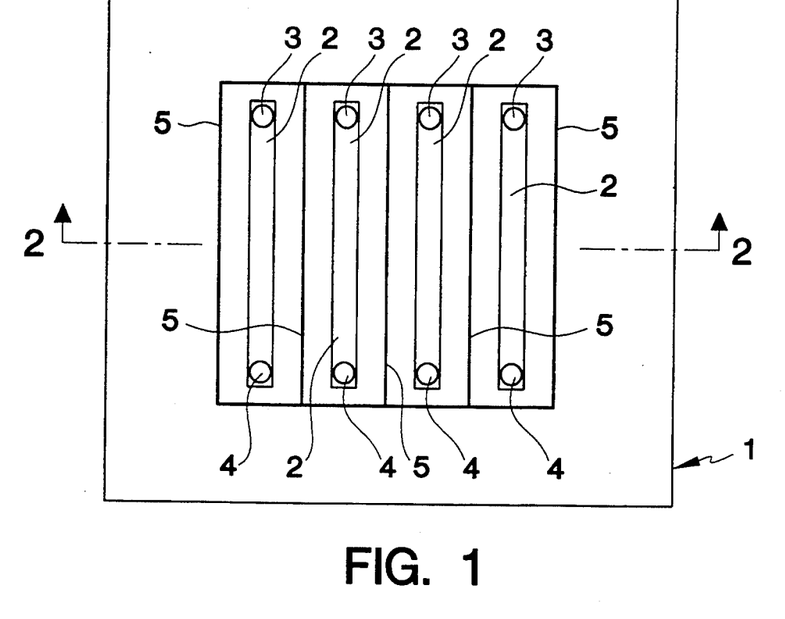
FIG. 1 is a schematic transparent top plan view of an embodiment of a microfluidic flow cell block according to the present invention.
Figure 2:
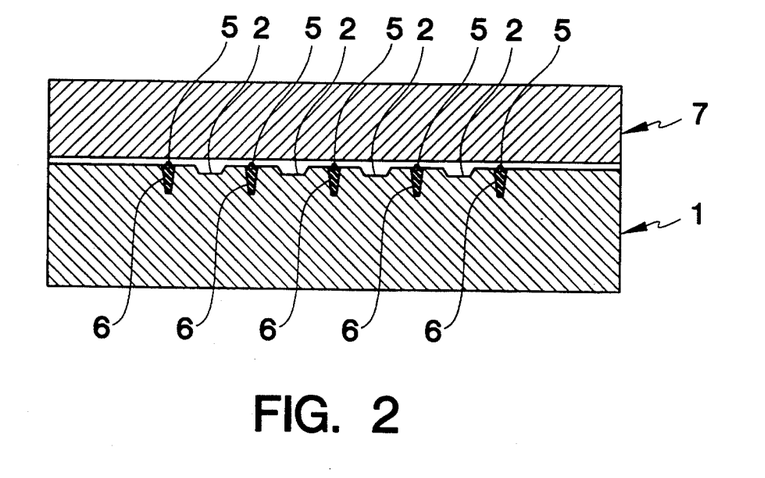
FIG. 2 is a sectional view of the flow cell block along 2—2 in FIG. 1.

FIGS. 1 and 2 are schematic illustrations of a microfluidic flow cell block, e.g. to be used in an optical biosensor instrument of the type described in the aforementioned WO 90/05295. It consists of a bottom plate 1 of a suitable hard material, for example silicon, into the upper surface of which there are recessed four upwardly open flow cell channels 2. The bottom of each flow cell channel 2 is provided at each end thereof with orifices 3 and 4 serving as fluid inlets and outlets, respectively. The orifices 3, 4 are connected to conduits not further illustrated in the figures, such as vertically extending riser ducts. Adjacent flow cell channels are separated by resilient sealing strips 5, e.g. of silicon rubber, moulded into respective grooves or recesses 6 in the bottom plate 1. As appears from FIG. 1 the sealing strips 5 also extend along the short ends of the flow cell channels such that each flow cell channel 2 is surrounded by a sealing strip. To complete the flow cells a top plate 7 is placed against the bottom plate 1. For purposes of illustration only the top plate 7 is shown in FIG. 2 as resting upon the resilient sealing strips 5, but in the actual practice the bottom and top plates 1, 7 are pressed against each other to compress the sealing strips 5 and bring the opposed plate surfaces in mutual contact to complete the respective flow cells as will be described below.

Figure 3:
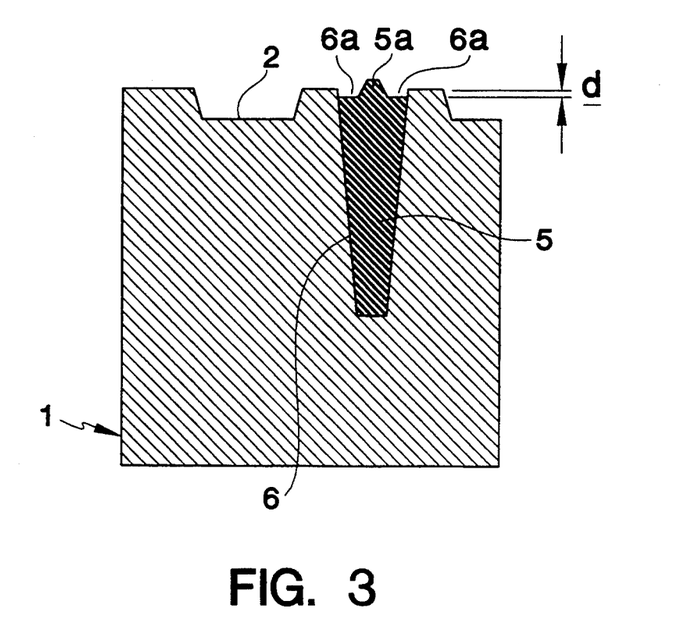
FIG. 3 is a sectional partial view of the bottom part of the flow cell block in FIGS. 1 and 2.
Figure 4:
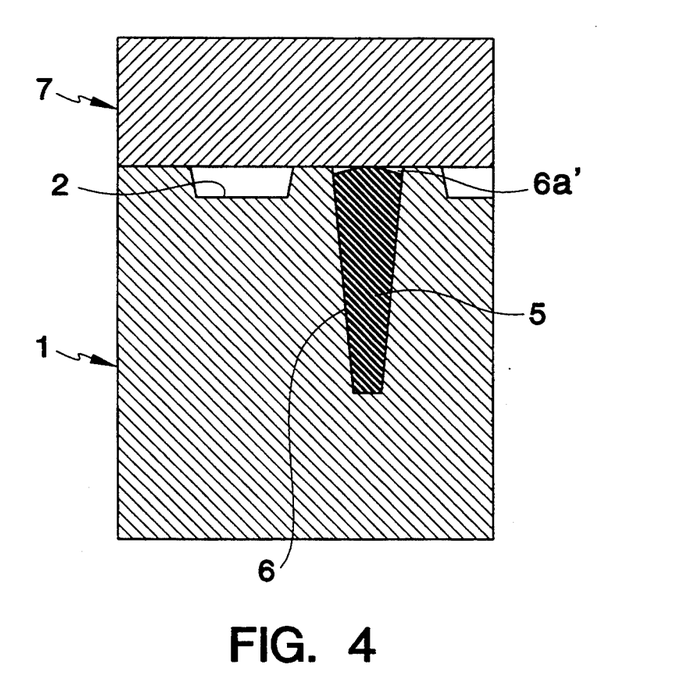
FIG. 4 is a corresponding view as in FIG. 3 with the complete flow cell block in FIGS. 1 and 2.

Although not shown in FIG. 2, to permit the necessary compression of each sealing strip 5, the top part thereof is configured not to fill up the groove 6 completely in order to leave sufficient space for accommodating the deformed sealing material. Thus, with reference to FIG. 3 the top part 5a of the sealing strip 5 is formed as a ridge or the like which is thinner than the base part of the member 5 and extends from a distance d below the upper edge of the groove 6. Thereby an interspace 6a with respect to the groove wall is defined on either side of the top part 5a. When the sealing member 5 is deformed by pressing the plate 7 against the flow cell block 1, on one hand, the part 5a broadens, and, on the other hand, the surrounding material is pressed upwards. The deformed material portions are, however, completely accommodated in the above mentioned interspaces 6a as is illustrated in FIG. 4, thereby ensuring that the compressed sealing strip will not be forced in between the contacting surfaces of the bottom plate 1 and the top plate 7 but provide for efficient sealing between the flow cells simultaneously as allowing maximum contact of the respective contact surfaces. As is indicated in FIG. 4 a small gap 6a' will consequently remain between the sealing strip parts on either side of the ridge 5a and the top plate 7. In this manner efficient sealing will be obtained even in the case of very minute channel sizes, such as channel heights in the range of about 0.1 to about 10 micrometers.

For the above mentioned biosensor application the top plate 1 will comprise a sensing surface (not specifically shown) as the contact surface, the latter thereby forming the top wall of each complete flow cell.

As an example of the channel sizes contemplated herein, the flow cells illustrated in FIGS. 1 and 2 may have a width of about 300 micrometers, a length of about 2 millimeters and a height typically in the range of about 5 to 50 micrometers.

The channels 2 and 5 in the bottom plate 1 illustrated in FIGS. 1 and 2 may be produced by per se conventional techniques. Thus, in case the plate is of silicon, the grooves or channels may be produced by chemical etching. Since the flow cells and the sealing material grooves have different depths two sequential etching operations will be required. This may be performed as follows.

The plate surface is first oxidized whereupon a photoresist is applied to the oxide layer, e.g. by spinning technique. A suitable oxide layer thickness for the present purposes may be about 8000 Å. A mask having the desired opening pattern for the sealing material grooves is then placed upon the surface and the bare photoresist portions are subjected to light exposure. After development causing the exposed portions of the photoresist to be removed and thereby bare the oxide layer, the bared oxide areas are etched and the remaining photoresist is dissolved and removed. By a first silicon etching procedure a first part of each sealing material groove 6 is then recessed. Following a second photoresist application the areas defining the flow cells are exposed through a corresponding mask. Development of the exposed photoresist, oxide etching, photoresist removal, and a second silicon etching will produce the flow cell channels 2 as well as the remaining depth of the sealing material grooves. In case three or more different channel depths are desired rather than two as described above, one may proceed in the same way as above, i.e. successively open region after region for etching without intermediate oxidation, the channel or groove which is desired to have the smallest depth being opened last for etching, the etching depth of the first opened area being the sum of all the etchings that the silicon plate has been subjected to. By appropriate selection of the etching times the resulting etching depths of the different etching steps may be varied. The above (in connection with FIGS. 1 and 2) mentioned riser ducts ending in the bottom openings 3 of the flow cell channels 2 are, for example, produced by laser drilling.

In an alternative procedure the flow cell channels 4 are first etched as above by the described process steps. The plate surface is then subjected to a renewed oxidation and all the steps are repeated for etching the sealing material grooves. In this way as low channel depths as will be desired may be produced. Thus, while the first mentioned method with a single oxidation conveniently permits channel depths down to about 5 $\mu$m to be produced, as small channel depths as, say, 0.1 $\mu$m may be obtained by the last-mentioned method.

Figure 5:
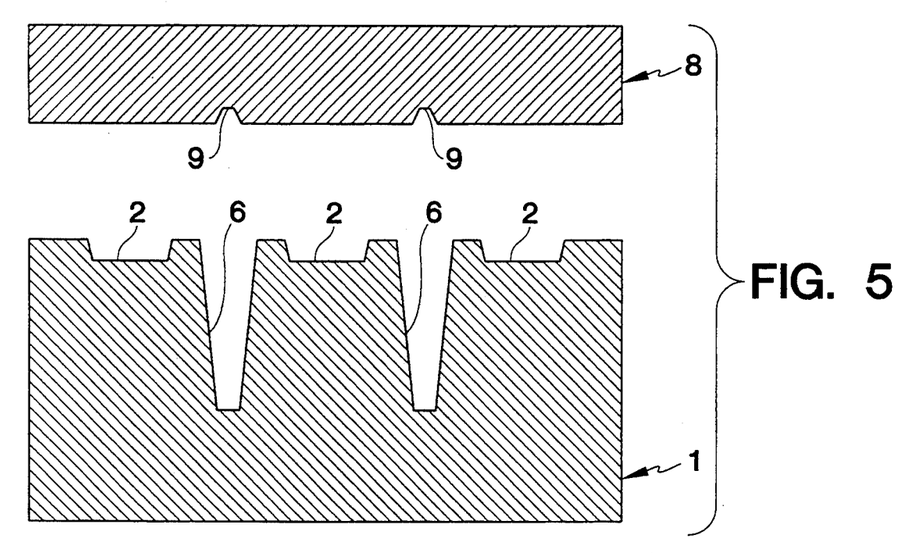
FIG. 5 is a schematic sectional view of a flow cell block member having recesses for sealing material, and separated therefrom a counter mould for forming mould cavities with the flow cell block member.

FIG. 5 illustrates a flow cell bottom plate 1 corresponding to that in FIGS. 1 and 2 but which for ease of illustration, however, has only three flow cell channels 2 and two sealing material grooves 6 which may have been obtained by one of the etching procedures just described. Also illustrated in the figure is a counter mould plate 8, having two grooves 9 of a smaller size as compared with grooves 2 and 6 of the plate 1 and designed to be aligned with the sealing material grooves 6 when the counter mould 8 is correctly applied to the flow block 1. The counter mould 8 may, for example, also be of silicon with the grooves 9 produced by etching as above. It may, however, alternatively at least partially be made of an elastomeric material as will be described below.

Figure 6:
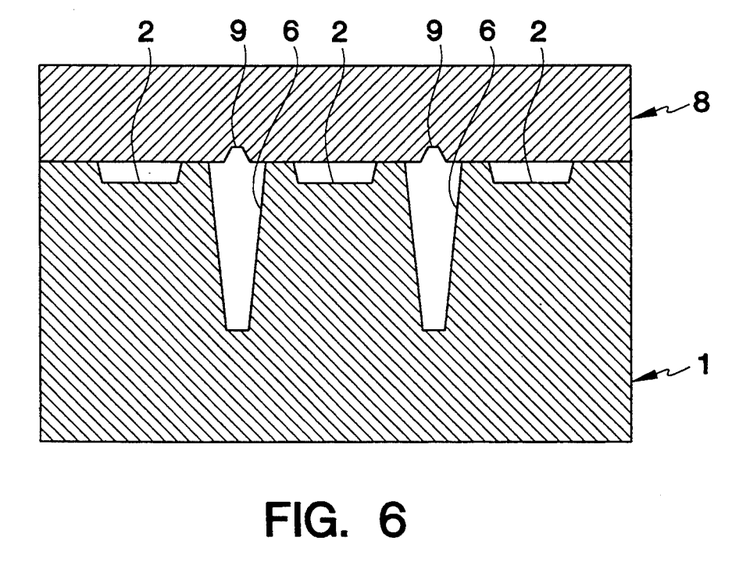
FIG. 6 is a corresponding view as in FIG. 5 with the flow cell block member and counter mould brought together.

FIG. 6 shows the counter mould 8 applied to the flow cell bottom plate 1, the sealing material grooves 6 of the latter and the grooves 9 of the counter mould 8 together defining mould cavities for sealing material to be injected into them.

Figure 7:
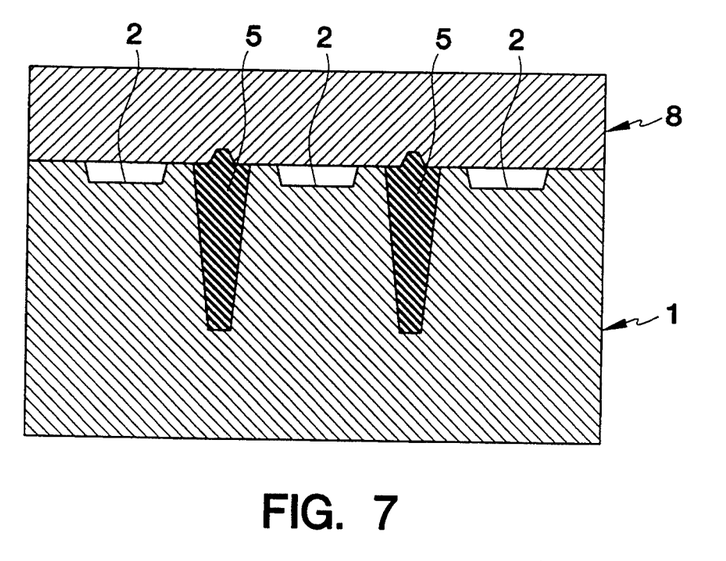
FIG. 7 is a corresponding view as in FIG. 6 with sealing material injected into the mould cavities.

In FIG. 7 a fluid sealing material 5 has been injected into the mould cavities 6, 9. The sealing material may, for example, be a fluid cross-linkable silicone rubber. A commercially available silicone rubber containing an initiator and useful for the purposes of the present invention is supplied by General Electric Company under the designation RTV 670. Prior to injecting the fluid silicone rubber the counter mould surface is treated with a release agent. After the silicone liquid has been injected it is hardened or cured, either by itself at ambient temperature when it contains an initiator, or by external means, such as UV light or electron beam curing, whereupon the counter mould is removed.

Figure 8:
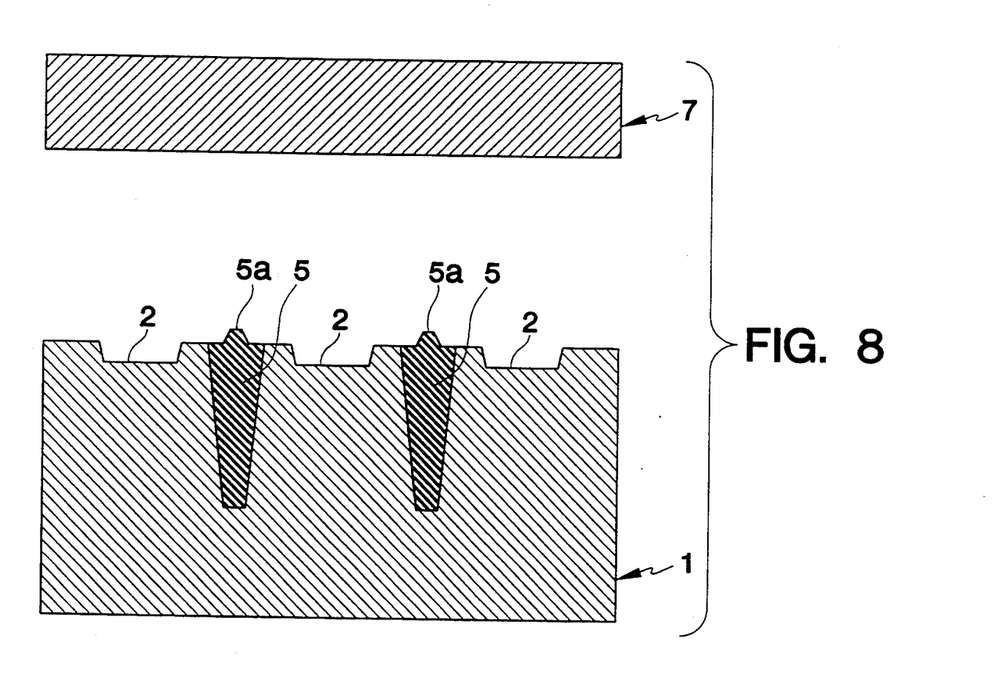
FIG. 8 is a sectional view of the flow cell block in FIG. 7 with the counter mould removed and a top plate member to be applied against it.
Figure 9:
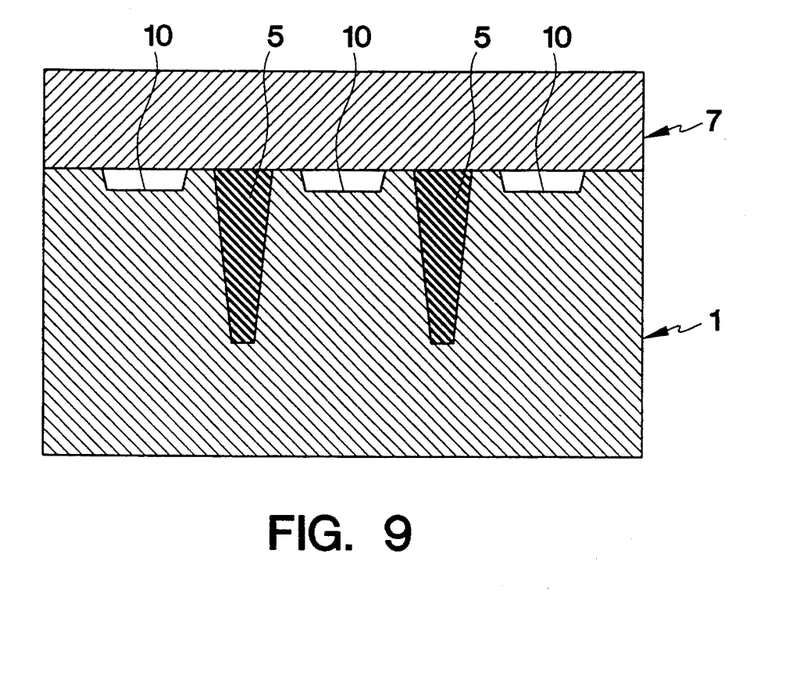
FIG. 9 is a corresponding view as in FIG. 8 with the top plate applied to the flow cell block member.

The resulting flow cell block is shown in FIG. 8. It thus consists of a rigid plate 1 having three parallel flow cell channels 2 separated by two resilient sealing strips 5, the top portions 5a of the latter projecting above the plate surface. Due to a certain shrinkage in connection with the hardening or curing of the sealing material the sealing strip 5 will, however, have the slightly vertically contracted configuration in the top part thereof as is illustrated in FIG. 3 and which is necessary for the desired function of the sealing. The extent of this shrinkage is inter alia determined by the height of groove 6. The latter height will also determine the resistance to compression. By proper selection of the heights of sealing material groove 6 and counter mould groove 9 it is thus possible to obtain a suitable protrusion 5a as well as a suitable deformation space (distance d in FIG. 3) for the desired sealing properties to be obtained. In the microsize contexts contemplated herein, i.e. flow cell channel depths of about 0.1 to about 500 $\mu$m, while the extension of the projecting part 5a of the sealing strip depends on the flatness of the plate to be applied against it, an exemplary extension in the case of the latter plate being for instance of a standard float glass is about 2.5 $\mu$m. Upon the application of a rigid top plate member 7, e.g. a plate supporting a sensing surface in case of use in connection with a biosensor as mentioned previously, the sealing strip protrusions are compressed such that the opposed surfaces contact each other, as is illustrated in FIG. 9. Thereby three flow cells 10 are defined by the channels 2 and the plate member 7, which flow cells are efficiently sealed off from each other in respect of fluid leakage by the two sealing strips 5 as has been explained above.

Figure 10:
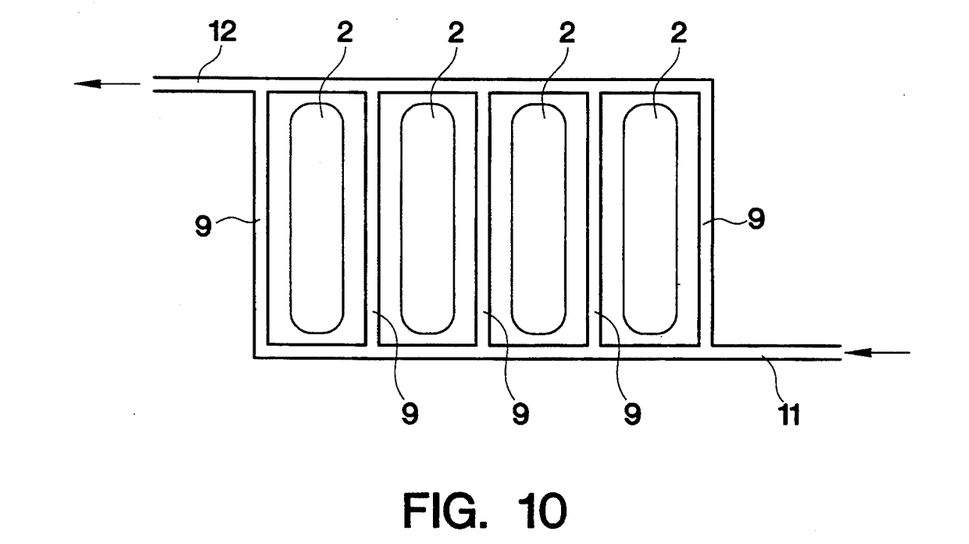
FIG. 10 is a schematic transparent view from above of a sheet of a set of flow cell block/counter mould units permitting the resilient sealings to be moulded simultaneously for the whole set.

FIG. 10 illustrates schematically an embodiment of a channel system for the counter mould 8 for the injection of fluid sealing material into the sealing material grooves 6. In the illustrated case five parallel grooves 9, corresponding to the top parts of the sealing strips 5 to be moulded, each extend between a common inlet channel 11 and a common outlet channel 12. With the counter mould properly applied to the flow cell bottom plate 1 (e.g. by means of guide pins or the like) the grooves 9 will extend centrally above the aforementioned grooves 6 and between the flow cell channels 2, indicated by thin lines. It is realized that when fluid sealing material is injected into inlet channel 11, it will successively fill the sealing strip cavities and then exit through the outlet channel 12. It will readily be appreciated that a plurality of counter mould units such as shown may be connected in series and/or in parallel in one single sheet to be applied to a corresponding flow cell bottom sheet having a plurality of sets of flow cell channels and sealing material grooves. After injection and curing of the fluid sealing material, the counter mould plate is removed and the individual flow cell blocks are cut out.

When the above described microfluidic system is used in connection with an optical biosensor of the aforementioned type, plate 7 in FIG. 2 is of glass and is covered by a thin film of, for example, gold. P-polarized incident light coupled to the lower surface of the sensor plate 7 through a prism (not shown) is totally internally reflected at the glass-metal interface, an intensity dip appearing in the reflected light at a specific angle of reflectance due to surface plasmon resonance (SPR). The angle will vary with the refractive index of the solution close to the metal film, and by measuring the displacement of the reflectance minimum, the extent of changes in surface concentration of biomolecules may be determined. In this manner e.g. an immunoassay for an analyte in a solution may be performed by immobilizing an antibody to the metal surface, passing the sample over the surface and measure the change in resonance angle caused by the binding of analyte to the immobilized antibody.

If the sealing strips 5 in FIGS. 1 and 2 are of a material having a refractive index within the measuring range of the biosensor instrument, the reflected light from the metal surface opposite to the sealing strip may be used as a temperature reference, since the refractive index of the material will vary with the temperature and thereby be representative thereof. This may, for example, be used for controlling the necessary thermostating means.

Figure 11:
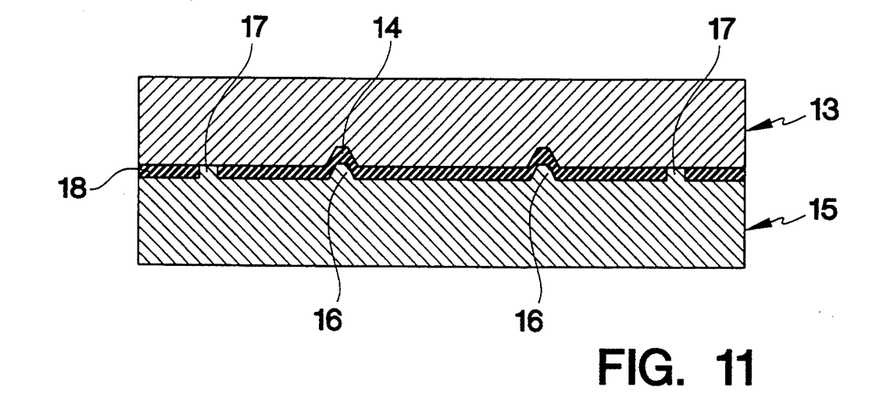
FIG. 11 is a sectional view of a modified counter mould applied to a mould plate for forming an elastic layer on the counter mould surface.
Figure 12:
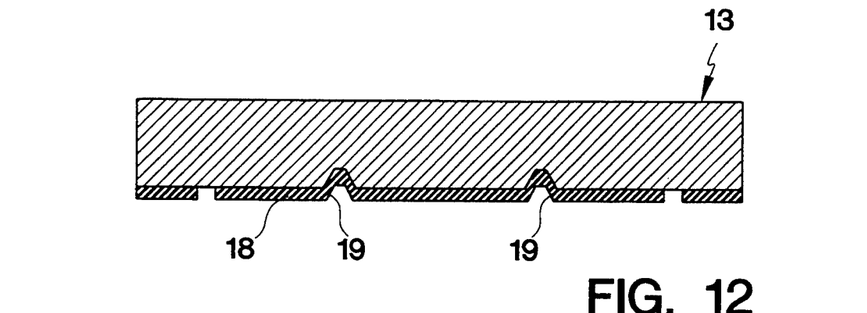
FIG. 12 is a sectional view of the elastic layer coated counter mould formed in FIG. 11.
Figure 13:
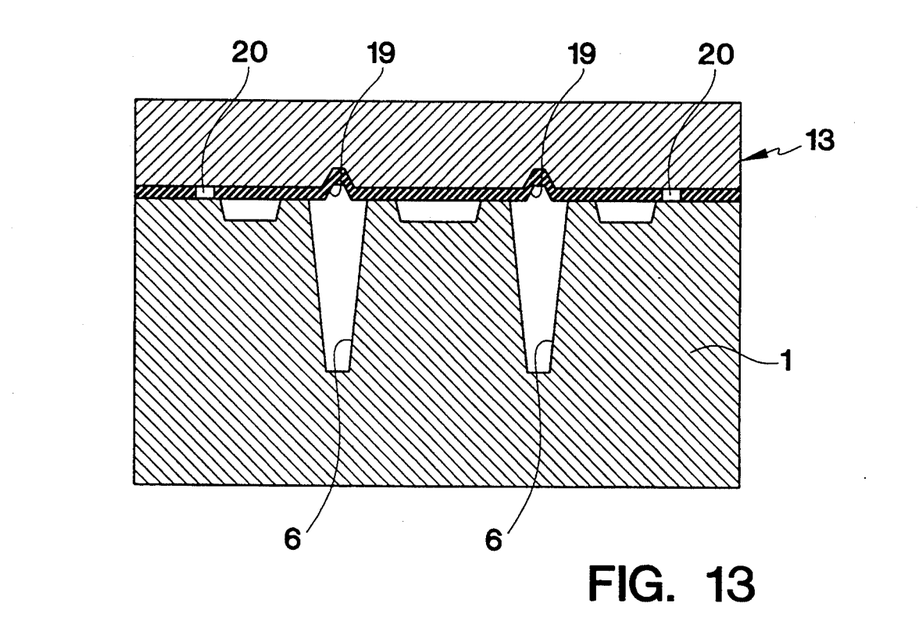
FIG. 13 is a corresponding view as in FIG. 6 but including the modified elastic layer coated counter mould of FIG. 12.

The use in the method of the present invention of a modified counter mould having an elastic surface coating layer is illustrated in FIGS. 11 to 13. FIG. 11 schematically illustrates the manufacture of such a modified counter mould and shows a counter mould member 13 having two parallel grooves 14 which is applied to a mould plate 15 having protrusions or ridges 16 of a corresponding extension as the grooves 14. The ridges 16 are designed to define grooves in the elastic counter mould surface to be produced corresponding to grooves 9 in FIG. 6. Spacing means 17 extend from the surface of the mould plate 15 to keep the two mould members 13, 15 spaced from each other to define a mould gap therebetween. This mould gap has in FIG. 11 been filled with a fluid sealing material 18, such as a cross-linkable silicone rubber. When the sealing material 18 has hardened the counter mould 13 is removed from mould plate 15. FIG. 12 shows the resulting counter mould exhibiting an elastomeric mould surface with grooves 19 therein.

FIG. 13 illustrates the modified counter mould 13 applied to the flow cell bottom plate 1 of FIG. 6, for example. In comparison with the FIG. 6 embodiment the counter mould 13 has an elastic surface with grooves 19 corresponding to grooves 9 in FIG. 6. Reference numeral 20 designates cavities resulting from the spacing means 17 in FIG. 11.

Such a counter mould having an elastic mould surface is advantageous especially in that the surface smoothness requirements on the flow cell bottom plate 1, e.g. of silicon, may be reduced, and that the channels 6 may be arranged more closely, i.e. with smaller interspaces.

The invention is, of course, not restricted to the embodiments specifically described above and illustrated in the drawings, but many modifications and changes are possible within the scope of the present inventive concept as defined in the following claims.

I claim:

1. A method for producing a leakage-proof sealing means in a microfluidic channel assembly comprising first and second flat surface members which when pressed against each other define at least part of a microfluidic channel system between them, which method comprises the steps of
   (i) recessing at least one groove structure into a flat surface of the first flat surface member;
   (ii) providing a counter mould, the mould surface of which has at least one groove structure or at least one ridge structure, said structure or structures having an extension corresponding to, but a smaller width than, the groove structure or structures of the first member;
   (iii) applying the counter mould against the first member to define a mould cavity or cavities by the groove structure or structures of the first member with the counter mould portions comprising said groove or ridge structure or structures;
   (iv) introducing a fluid sealing material, capable of hardening to form a resilient sealing structure, into the mould cavity or cavities; and
   (v) after hardening of the fluid sealing material, removing the mould from the first member;
   the top part of the mould cavity or cavities being configured in dependence of the shrinkage or expansion properties of the fluid sealing material whereby the resulting moulded resilient sealing structure projects above groove edges of the first member while leaving sufficient space in an upper part of said groove to permit complete accommodation therein of a deformed top part of the resilient sealing structure when compressed by the second member.

2. A method according to claim 1, characterized in that it further comprises the step of recessing a fluid channel groove structure into said first member.

3. A method according to claim 2, characterized in that said fluid channel groove structure is recessed simultaneously as said groove structure for the sealing material.

4. A method according to claim 1, characterized in that said fluid sealing material when hardening is capable of shrinking to an extent sufficient for providing said required space or spaces in the upper part of the sealing material groove.

5. A method according to claim 1, characterized in that the mould surface of said counter mould is elastic.

6. A microfluidic system device comprising a first member of a substantially rigid material having a substantially flat surface and designed to be applied to a substantially flat surface of a second member of a substantially rigid material, one or both of the surfaces of said members being provided with a first groove structure wherein a corresponding fluid channel system is defined between the members when applied to each other, characterized in that said first member includes at least one second groove structure having a resilient sealing means moulded into it for sealing off parts of said fluid channel system from adjacent areas, a top portion of said sealing means projecting above the surface of said first member and being spaced from at least one side edge of said second groove structure wherein the top portion is capable of being substantially accommodated in the groove space when it is deformed by the application of said two members against each other.

7. A microfluidic system device according to claim 6, characterized in that both said first and second groove structures are provided in said first member.

8. A microfluidic system device according to claim 6, characterized in that it comprises at least two separate fluid channel grooves each of which is individually enclosed by said sealing means.

9. A microfluidic system device according to claim 6, characterized in that it also comprises said second member.

10. A microfluidic system device according to claim 6, characterized in that at least said first member is made of silicon.

11. A microfluidic system device according to claim 6, characterized in that at least part of said first groove structure has a maximum height of about 50 micrometers.

12. A microfluidic system device according to claim 6, characterized in that said resilient sealing material comprises silicone rubber.

13. A microfluidic system device according to claim 6 for use in a surface plasmon resonance based optical biosensor apparatus, characterized in that said second member is a substantially flat member supporting a sensing surface.

14. A microfluidic system device according to claim 13, characterized in that at least part of said sealing means has a refractive index permitting it to serve as a temperature reference.

15. A microfluidic system device according to claim 11, wherein said first groove structure has a height of approximately 10 micrometers.

* * * * *